United States Patent [19]

Pelyva et al.

[11] Patent Number: 4,859,772
[45] Date of Patent: Aug. 22, 1989

[54] PROCESS FOR THE PREPARATION OF 3-ISOPROPYL-BENZO-2-THIA-1,3-DIAZI-NONE-(4)-2,2-DIOXIDE

[75] Inventors: Jenö Pelyva; K. István Vecsey, both of Füzfogyártelep; Zoltán Kolonics, Balatonalmádi; Lászlo Légrádi, Füzfogyártelep; Lajos Nagy, Füzfogyártelep; András Horváth, Füzfogyártelep; Ferenc Fodor, deceased, late of Füzfogyártelep, by Edit Tavasz Fodor née Ibolyka, heir; Csaba Soptei, Veszprém; Dezso Sebok, Veszprém; Elemér Tömördi, Veszprém; László Lendvai, Balatonfüzfo; Béla Karácsonyi, Budapest; Erzsébet Diószegi, Veszprém, all of Hungary

[73] Assignee: Nitro Kémia Ipartelepek, Füzfogyártelep, Hungary

[21] Appl. No.: 105,230
[22] PCT Filed: Dec. 3, 1986
[86] PCT No.: PCT/HU86/00065
  § 371 Date: Jul. 15, 1987
  § 102(e) Date: Jul. 15, 1987
[87] PCT Pub. No.: WO87/03588
  PCT Pub. Date: Jun. 18, 1987

[30] Foreign Application Priority Data

Dec. 3, 1985 [HU] Hungary .................... 4615/85

[51] Int. Cl.$^4$ ............................ C07D 285/16
[52] U.S. Cl. ................................... 544/11
[58] Field of Search ..................... 544/8, 11

[56] References Cited

U.S. PATENT DOCUMENTS

| | | |
|---|---|---|
| 3,822,257 | 7/1974 | Hamprecht et al. ............... 544/11 |
| 3,935,201 | 1/1976 | Mangold et al. .................. 544/11 |
| 4,139,700 | 2/1979 | Kloek ............................. 544/11 |
| 4,208,514 | 6/1980 | McKendry et al. ............... 544/11 |

*Primary Examiner*—John M. Ford
*Attorney, Agent, or Firm*—Birch, Stewart, Kolasch & Birch

[57] ABSTRACT

The present invention relates to a process for the preparation of 3-isopropyl-benzo-2-thia-1,3-diazinone-(4)-2,2-dioxide which comprises preparing isopropyl sulfamoyl chloride in one step by reacting N,N'-diisopropyl-urea with phosphorus trichloride and chlorine in the presence of oleum and sulfuric acid and condensing the so obtained isopropyl sulfamoyl chloride at room temperature without any solvent in the presence of an excess of N,N-diethyl aniline with anthranylic acid methyl ester and subjecting the thus obtained N-isopropyl-N'-o-carbomethoxy-phenyl-sulfamide to cyclization in the presence of sodium methylate, extracting the obtained crude 3-isopropyl-benzo-2-thia-1,3-diazinone-(4)-2,2-dioxide with a mixture of methanol and water and after adding water to the aqueous-methanolic mixture and sedimenting the contaminations isolating a product of high purity.

2 Claims, No Drawings

PROCESS FOR THE PREPARATION OF 3-ISOPROPYL-BENZO-2-THIA-1,3-DIAZINONE-(4)-2,2-DIOXIDE

The present invention is related to the preparation of the known contact herbicidally active 3-isopropyl-benzo-2-thia-1,3-diazinone-(4)-2,2-dioxide (bentazone). The preparation and use of bentazone is disclosed in DAS Nos. 1 542 836 and 2 105 687.

According to the state of art and industrial experiences the bentazone can be best prepared by using as the starting material an anthranylic acid alkyl ester by reacting the same with isopropyl sulfamoyl chloride and after condensation and cyclization the end product may be isolated. Condensation and cyclization may be carried out in one step, i.e. the condensed product need not be isolated. This process is disclosed in detail in German Patent Specification No. 2 357 063, according to which anthranylic acid methyl ester is reacted with isopropyl sulfamoyl chloride in toluene at 60° C. in the presence of tri-n-butyl amine as an acid binding agent. The thus obtained product is then subjected to cyclization without isolating the intermediate product in the presence of NaOCH₃ within 1 hour at 60°–80° C. Yield: 93%, melting point of the obtained bentazone: 130°–132° C.

The drawback of the known process is the necessity of the intermediate isopropyl sulfamoyl chloride for the synthesis. The preparation of this intermediate product is accompanied by severe difficulties on an industrial scale. This is why an adduct of picoline and SO₃ is used instead of sulfamoyl chloride according to German Patent Specification No. 2 710 382 and European Patent Specification No. 70 147, by reacting anthranylic acid isopropyl amide with an adduct of SO₃ and picoline, resulting in 1-(isopropyl-amido-carbonyl)-phenylsulfamic acid and by converting same to bentazone in the presence of POCl₃ while eliminating water.

The preparation of isopropyl-sulfamoyl chloride is discussed by G. Hamprecht et al. in Angewandte Chemie (93, 151–163, 1981).

In German Patent Specification No. 2 164 197 a process is suggested for the preparation of N-alkyl-sulfamidic acid starting from the corresponding alkyl isocyanate by reacting the same with sulfuric acid. The obtained sulfamidic acid is chlorinated with PCl₅ in chloroform according to German Patent Specification No. 2 164 176 and the end product being isopropyl sulfamoyl chloride is distilled in vacuo. The yield of the chlorination amounts to 85.5, the yield of the preparation of Nalkyl-sulfamidic acid is not given.

According to German Patent Specification No. 2 424 371 isopropyl sulfamidic acid is prepared by reacting N,N'-diisopropyl-urea in an organic solvent with sulfur trioxide in the first step and with sulfuric acid in the second step. A disadvantage of this process is the necessity of a significant molar excess of sulfur trioxide and its disposal is also problematic, further the preparation of SO₃ from oleum by distillation or with inert gas demands an expensive apparatus.

According to German Patent Specification No. 2 852 274 alkyl sulfamoyl chloride is prepared by converting alkyl isocyanate or dialkyl urea with oleum or sulfuric acid to alkyl sulfamidic acid then with chlorinating agents in one step to alkyl sulfamoyl chloride. The preparation of isopropyl sulfamoyl chloride is not disclosed, only the chlorination step is described which can be performed with a yield of 76%. The quality of the end product is not disclosed.

Summarizing the methods for the preparation of bentazone one can see that only some steps of the several step - synthesis methods are dealt with and that the quality of the end product is not appropriate.

In German Patent Specifications Nos. 2 105 687 and 2 357 063 the condensation of isopropyl sulfamoyl chloride and anthranylic acid or ester and the subsequent cyclization are disclosed. The end product melts at 124°–132° C.

Bentazone prepared according to German Patent Specification No. 1 542 836 has to be purified. The purification of the crude bentazone is described in German Patent Specification No. 2 316 292 by dissolving the product in a first step in chlorobenzene and then extracting the basic contaminations with dilute hydrochloric acid and extracting bentazone with alkaline water in a second step followed by precipitation with acid.

In the known bentazone synthesis methods one tried to start from pure phase products in the individual steps, however, bentazone which could be used without further purification could be not prepared. The purification steps are accompanied with great losses and are expensive if the so far known methods are applied.

The object of the present invention was to find an improved process suitable for the economical preparation of bentazone of high purity which can be used without further purification.

According to the present invention the crude isopropyl sulfamoyl chloride obtained from N,N'-diisopropyl-urea with oleum and sulfuric acid and a mixture of PCl₃+Cl₂, can be reacted with anthranylic acid methyl ester without any solvent in the presence of N,N-diethyl aniline and can be converted to bentazone during cyclization with sodium methylate. The method according to the invention elaborated for the preparation of isopropyl sulfamoyl chloride shows—when comparing it with the state of art—a good yield and good quality even though the end product is not purified by vacuo distillation. Thus, the yield of the process disclosed in German Patent Specification No. 2 513 997 (1976) wherein isopropyl sulfamoyl chloride is distilled in vacuo, amounts only to 70% and yields of the processes of German Patent Specifications Nos. 2 514 646 (1976) and 2 514 937 (1976) are even lower: 63% and 60% resp. In the latter processes the end product is also purified by distillation in vacuo.

According to German Patent Specification No. 2 164 173 (1973) a yield of 85% was achieved by using isopropyl sulfamidic acid and PCl₅ in chloroform. Similarly vacuum distillation was used. Sulfonation and the preparation of the acid chloride is carried out in one step in German Patent Specification No. 2 852 274 in case of methyl sulfamoyl chloride in a yield of 85.2%. Isopropyl sulfamoyl chloride is prepared from isopropyl sulfamidic acid with a yield of 76%.

When comparing our process with the above mentioned processes the yield of the process according to the invention amounts to 92% and the quality of the product without vacuum distillation is as good as 90%.

According to German Patent Specification No. 2 357 063 the condensation of anthranylic acid ester and isopropyl sulfamoyl chloride is carried out in an inert organic solvent, e.g. in toluene in the presence of tri-n-butyl amine at 60° C. According to the process of the present invention the reaction is conducted without any solvent in the presence of N,N-diethyl aniline at room temperature. This not only advantageous because of the fact that no inert organic solvent is needed, but also due to the circumstance that N,N-diethyl-aniline-hydrochloride formed by binding the hydrochloric acid does not precipitate from the solution like in the inert organic solvent and thus a homogeneous solution is obtained.

As opposed to the use of tri-n-butyl amine or triethyl amine there is a further advantage, i.e. the condensation can be performed at room temperature instead of 60° C. mentioned in the example of the German specification. Thus, the detrimental effect of the higher temperature can be avoided.

If a product of extremely high purity is needed then the obtained bentazone has to be purified. According to the purification method elaborated for bentazone the contaminations of bentazone, the unreacted phase products are less soluble in aqueous methanol than pure bentazone and can be thus separated. According to German Patent Specification No. 2 316 292 purification is performed by alkaline or acidic treatment. The disadvantage of this method lies in the fact that contaminations which behave similarly to bentazone can be separated only with difficulties.

Summarizing the advantages of our process as compared with the known processes the following items can be listed:

(1) The preparation of isopropyl sulfamoyl chloride can be carried out in one step starting from N,N'-diisopropyl urea.

(2) The purification of isopropyl sulfamoyl chloride can be eliminated (distillation in high vacuo). Thus the process becomes more economic.

(3) Reaction of isopropyl sulfamoyl chloride and anthranylic acid can be carried out without any inert solvent and thus the recovery of the solvent is eliminated.

(4) Hydrochloric acid formed in the condensation of isopropyl sulfamoyl chloride with anthranylic acid ester is bound by N,N-diethyl aniline, the hydrochloride of which is dissolved in the given medium but does not dissolve in an inert solvent, thus the reaction velocity is increased due to the homogeneous medium.

(5) Condensation of isopropyl sulfamoyl chloride and anthranylic acid ester takes place at room temperature in the presence of N,N-diethyl aniline due to the homogeneous reaction mixture, thus the reaction at 60° C. is eliminated thus saving energy and avoiding the damage to the end product.

(6) A purer end product is obtained due to the previous technological steps as opposed to the known processes.

(7) Bentazone of high purity may be obtained by extraction with a mixture of methanol and water.

EXAMPLE 1

Isopropyl sulfamoyl chloride

To a suspension of 1 1 dichloroethane and 145 g (1.007 mole) of N,N'-diisopropyl urea, 150 g 56% oleum (1.05 mole $SO_3$) are added in about 15 minutes at 0°–5° C. The mixture is kept at this temperature for 30 minutes whereafter 30 g 100% sulfuric acid are added. The mixture is slowly heated to 80° C. during gas evolution. The mixture is then heated under reflux for 2 hours until gas evolution ceases.

The mixture is then cooled to 50° C. and then 285 g (2.07 mole) of phosphorous trichloride are added and chloride gas is introduced at a rate of 70–80 l/hour at 55°–65° C. during heat evolution. Chlorination lasts for about 1 hour. The product becomes a light clear solution. The solvent and $POCl_3$ are removed at 200 Hgmm to 80° C. and at 10 Hgmm to 90° C. 324 g of the product are obtained. Chlorine content: 20.32% (theoretical chlorine content: 22.53%). On the basis of the chlorine content the purity of the product is of 90%, yield: 92%.

EXAMPLE 2

(a) N-Isopropyl-N'-o-carbomethoxy-phenyl-sulfamide 75 g (0.5 mole) N,N-diethylaniline and 30.8 g (0.2 mole) 98–99% anthranylic acid methyl ester are admixed and to this mixture 34.7 g (0.2 mole) of 90% sulfamoyl chloride are added while stirring at 20°–30° C. and the homogeneous reaction mixture is stirred at this temperature for 15 minutes. Thus, the condensation reaction takes place.

(b) Cyclization of N-isopropyl-N'-o-carbomethoxy-phenyl-sulfamide to bentazone To a solution of N-isopropyl-N'-o-carbomethoxy-phenyl sulfamide obtained as given above in N,N-diethyl aniline 85 g 30% sodium methylate are added. The mixture is then stirred for 1–2 hours, methanol is distilled off and the mixture is cooled by adding 200 ml of water. N,N-diethyl aniline in a separate layer is separated from the aqueous layer. The aqueous layer is added to 100 g 15% hydrochloric acid while stirring at 20°–30° C. whereupon bentazone is precipitated. The precipitate is filtered, washed with water and dried. 47 g of the product are obtained, melting at 136°–139° C., content 96.8% determined by liquid chromatography, yield: 95.4%.

EXAMPLE 3

Comparative example according to German Patent Specification No. 2 357 063 (1975)

In an apparatus equipped with a stirrer 8.25 parts of toluene are admixed with 3.8 parts of anthranylic acid methyl ester and 4.8 parts of tri-n-butyl amine and to the mixture 3.95 parts of isopropyl sulfamoyl chloride are added at 20°–40° C. The mixture is then stirred for 1 hour at 60° C. and finally a solution of 10 parts (30% by mass) sodium methylate in methanol is added slowly. The mixture is stirred for a further hour at 60°–80° C. and methanol is then distilled off. The mixture is cooled to room temperature and 12 parts of water are added while cooling and the two layers are separated.

Sodium salt of 3-isopropyl-benzo-2-thia-1,3-diazinone-(4)-2,2-dioxide is dissolved in the aqueous layer. The aqueous layer is acidified to pH=1 by adding sulfuric acid. After filtration and drying 5.7 parts of 3-isopropyl-benzo-thia-1,1-diazinone-(4)-2,2-dioxide are obtained, melting point: 130°–132° C., yield: 93%.

After drying the organic layer is again led back to the reaction and distilled. According to our tests the obtained product is of 90% purity.

EXAMPLE 4

Preparation of 3-isopropyl-benzo-2-thia-1,3-diazinone-(4)-2,2-dioxide of high purity 100 g of crude bentazone (96%) are dissolved in 200 ml anhydrous methanol. To the obtained alcoholic solution 200 ml (80° C.) warm water is added while stirring and the mixture is stirred for 5 minutes. The stirrer is then stopped and the mixture is allowed to precipitate and sedimentate for 15 minutes. The solution is then isolated by suction and poured while stirring and cooling into 400 ml of water. After 15 minutes the precipitated product is filtered, washed with water and dried. Yield: 94 g, m. p.: 138°–139° C., purity: 99% analyzed by liquid chromatography.

We claim:

1. In a process for the production of 3-isopropyl-benzo-2-thia-1,3-diazinone-(4)-2,2-dioxide, which comprises reacting isopropyl sulfamoyl chloride with anthranylic acid methyl ester, and subjecting the thus obtained N-isopropyl-N'-o-carbomethoxyphenyl-sulfamide to cyclization in the presence of sodium methylate, to obtain 3-isopropyl-benzo-2-thia-1,3-diazinone-(4)-2,2-dioxide, the improvement comprising preparing isopropyl sulfamoyl chloride in one step by reacting N,N'-diisopropyl urea with phosphorus trichloride and chlorine in the presence of oleum and sulfuric acid, whereby a 3-isopropylbenzo-2-thia-1,3-diazinone-(4)-2,2-dioxide of high purity is obtained.

2. In a process for the production of 3-isopropyl-benzo-2-thia-1,3-diazinone-(4)-2,2-dioxide, which comprises reacting isopropyl sulfamoyl chloride with anthranylic acid methyl ester, and subjecting the thus obtained N-isopropyl-N'-o-carbomethoxyphenyl-sulfamide to cyclization in the presence of sodium methylate, to obtain 3-isopropyl-benzo-2-thia-1,3-diazinone-(4)-2,2-dioxide, the improvement comprising:

preparing isopropyl sulfamoyl chloride in one step by reacting N,N'-diisopropyl urea with phosphorus trichloride and chlorine in the presence of oleum and sulfuric acid, condensing the so obtained isopropyl sulfamoyl chloride at room temperature without solvent in the presence of an excess of N,N'diethyl aniline with anthranylic acid methyl ester, subjecting the thus obtained N-isopropyl-N'-o-carbomethoxyphenyl-sulfamide to cyclization in the presence of sodium methylate, extracting the obtained crude 3-isopropyl-benzo-2-thia-1,3diazinone-(4)-2,2-dioxide with a mixture of methanol and water and isolating a product of high purity after adding water to the aqueous-methanolic mixture and sedimenting the contaminations.

* * * * *